United States Patent
Suslian et al.

(10) Patent No.: US 7,621,864 B2
(45) Date of Patent: *Nov. 24, 2009

(54) METHOD FOR TREATING URINARY INCONTINENCE IN WOMEN AND IMPLANTABLE DEVICE INTENDED TO CORRECT URINARY INCONTINENCE

(75) Inventors: Patrice Suslian, Gordes (FR); Emmanuel Delorme, Chalon sur Saone (FR)

(73) Assignee: Coloplast A/S, Humlebaek (DK)

( * ) Notice: Subject to any disclaimer, the term of this patent is extended or adjusted under 35 U.S.C. 154(b) by 1190 days.

This patent is subject to a terminal disclaimer.

(21) Appl. No.: 11/040,698

(22) Filed: Jan. 21, 2005

(65) Prior Publication Data

US 2005/0131274 A1 Jun. 16, 2005

Related U.S. Application Data

(60) Continuation of application No. 10/455,465, filed on Jun. 4, 2003, now abandoned, which is a division of application No. 10/092,069, filed on Mar. 5, 2002, now Pat. No. 6,638,211, which is a continuation of application No. PCT/FR01/02120, filed on Jul. 3, 2001, which is a continuation-in-part of application No. 09/661,620, filed on Sep. 14, 2000.

(30) Foreign Application Priority Data

Jul. 5, 2000 (FR) .................................. 00 08706

(51) Int. Cl.
*A61F 2/02* (2006.01)

(52) U.S. Cl. ....................................................... 600/30
(58) Field of Classification Search ............. 600/29–32, 600/37; 128/DIG. 25; 606/141
See application file for complete search history.

(56) References Cited

U.S. PATENT DOCUMENTS

| 2,738,790 A | 3/1956 | Todt, Sr. et al. |
| 3,124,136 A | 3/1964 | Usher |
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,924,633 A | 12/1975 | Cook et al. |
| 3,995,619 A | 12/1976 | Glatzer |

(Continued)

FOREIGN PATENT DOCUMENTS

DE 2 305 815 8/1974

(Continued)

OTHER PUBLICATIONS

Hardiman, et al. Cystocele repair using polypropylene mesh. Br. J. Obstet. Gynaecol. 107: 825-26 (2000).

(Continued)

*Primary Examiner*—John P Lacyk
(74) *Attorney, Agent, or Firm*—Daniel G. Chapik (57) ABSTRACT

The invention relates to a method and device for treating urinary incontinence in women.

11 Claims, 2 Drawing Sheets

U.S. PATENT DOCUMENTS

| | | | |
|---|---|---|---|
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogui et al. |
| 4,246,660 A | 1/1981 | Wevers |
| 4,441,497 A | 4/1984 | Paudler |
| 4,509,516 A | 4/1985 | Richmond |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,920,986 A | 5/1990 | Biswas |
| 5,013,292 A | 5/1991 | Lemay |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,188,636 A | 2/1993 | Fedotov |
| 5,207,694 A | 5/1993 | Broomé |
| 5,209,756 A | 5/1993 | Seedhom et al. |
| 5,250,033 A | 10/1993 | Evans et al. |
| 5,256,133 A | 10/1993 | Spitz |
| 5,281,237 A | 1/1994 | Gimpelson |
| 5,328,077 A | 7/1994 | Lou |
| 5,336,239 A | 8/1994 | Gimpelson |
| 5,337,736 A | 8/1994 | Reddy |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,507,796 A | 4/1996 | Hasson |
| 5,520,700 A | 5/1996 | Beyar et al. |
| 5,544,664 A | 8/1996 | Benderev et al. |
| 5,562,685 A | 10/1996 | Mollenauer et al. |
| 5,562,689 A | 10/1996 | Green et al. |
| 5,571,139 A | 11/1996 | Jenkins, Jr. et al. |
| 5,591,163 A | 1/1997 | Thompson |
| 5,611,515 A | 3/1997 | Benderev et al. |
| 5,628,756 A | 5/1997 | Barker, Jr. et al. |
| 5,633,286 A | 5/1997 | Chen |
| 5,669,935 A | 9/1997 | Rosenman et al. |
| 5,683,349 A | 11/1997 | Makower et al. |
| 5,807,403 A | 9/1998 | Beyar et al. |
| 5,836,314 A | 11/1998 | Benderev et al. |
| 5,836,315 A | 11/1998 | Benderev et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,934,283 A | 8/1999 | Willem et al. |
| 5,935,122 A | 8/1999 | Fourkas et al. |
| 5,944,732 A | 8/1999 | Raulerson et al. |
| 5,972,000 A | 10/1999 | Beyar et al. |
| 5,988,171 A | 11/1999 | Sohn et al. |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,039,686 A | 3/2000 | Kovac |
| 6,042,534 A | 3/2000 | Gellman et al. |
| 6,042,536 A | 3/2000 | Tihon et al. |
| 6,048,351 A | 4/2000 | Gordon et al. |
| 6,050,937 A | 4/2000 | Benderev |
| 6,053,935 A | 4/2000 | Brenneman et al. |
| 6,068,591 A | 5/2000 | Bruckner et al. |
| 6,071,290 A | 6/2000 | Compton |
| 6,074,341 A | 6/2000 | Anderson et al. |
| 6,106,545 A | 8/2000 | Egan |
| 6,110,101 A | 8/2000 | Tihon et al. |
| 6,117,067 A | 9/2000 | Gil-Vernet |
| 6,168,611 B1 | 1/2001 | Rizvi |
| 6,221,005 B1 | 4/2001 | Bruckner et al. |
| 6,273,852 B1 | 8/2001 | Lehe et al. |
| 6,302,840 B1 | 10/2001 | Benderev |
| 6,306,079 B1 | 10/2001 | Trabucco |
| 6,328,744 B1 | 12/2001 | Harari et al. |
| 6,334,446 B1 | 1/2002 | Beyar |
| 6,352,553 B1 | 3/2002 | van der Burg et al. |
| 6,382,214 B1 | 5/2002 | Raz et al. |
| 6,406,423 B1 | 6/2002 | Scetbon |
| 6,406,480 B1 | 6/2002 | Beyar et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,494,887 B1 | 12/2002 | Kaladelfos |
| 6,494,906 B1 | 12/2002 | Owens |
| 6,502,578 B2 | 1/2003 | Raz et al. |
| 6,530,943 B1 | 3/2003 | Hoepffner et al. |
| 6,575,897 B1 | 6/2003 | Ory et al. |
| 6,582,443 B2 | 6/2003 | Cabak et al. |
| 6,612,977 B2 | 9/2003 | Staskin et al. |
| 6,638,211 B2 * | 10/2003 | Suslian et al. ................ 600/30 |
| 6,786,861 B1 | 9/2004 | Pretorius |
| 2001/0000533 A1 | 4/2001 | Kovac |
| 2001/0018549 A1 | 8/2001 | Scetbon |
| 2001/0039423 A1 | 11/2001 | Skiba et al. |
| 2001/0049467 A1 | 12/2001 | Lehe et al. |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0082619 A1 | 6/2002 | Cabak et al. |
| 2002/0083949 A1 | 7/2002 | James |
| 2002/0091298 A1 | 7/2002 | Landgrebe |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0099260 A1 | 7/2002 | Suslian et al. |
| 2002/0103542 A1 | 8/2002 | Bilbo |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0119177 A1 | 8/2002 | Bowman et al. |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0183588 A1 | 12/2002 | Fierro |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0078468 A1 | 4/2003 | Skiba et al. |
| 2003/0100954 A1 | 5/2003 | Schuldt-Hempe et al. |
| 2003/0130670 A1 | 7/2003 | Anderson et al. |

| | | |
|---|---|---|
| 2003/0149440 A1 | 8/2003 | Kammerer et al. |
| 2003/0171644 A1 | 9/2003 | Anderson et al. |
| 2003/0176875 A1 | 9/2003 | Anderson et al. |
| 2003/0212305 A1 | 11/2003 | Anderson et al. |
| 2004/0097974 A1 | 5/2004 | DeLeval |
| 2004/0231678 A1 | 11/2004 | Fierro |
| 2004/0243166 A1 | 12/2004 | Odermatt et al. |
| 2004/0249240 A1 | 12/2004 | Goldmann et al. |
| 2005/0080317 A1 | 4/2005 | Merade |
| 2005/0107805 A1 | 5/2005 | Bouffier et al. |
| 2005/0240076 A1 | 10/2005 | Neisz et al. |

FOREIGN PATENT DOCUMENTS

| | | |
|---|---|---|
| DE | 4 220 283 | 12/1993 |
| DE | 4 304 353 | 4/1994 |
| EP | 0 470 308 | 2/1992 |
| EP | 0 643 945 | 3/1995 |
| EP | 0 650 703 | 5/1995 |
| EP | 1 093 758 | 4/2001 |
| GB | 378288 A | 8/1932 |
| RU | 2187251 C1 | 8/2002 |
| RU | 2196518 C2 | 1/2003 |
| SU | 1 225 547 | 4/1986 |
| SU | 1 342 486 | 10/1987 |
| SU | 1475607 A1 | 4/1989 |
| WO | WO 93/17635 | 9/1993 |
| WO | WO 93/19678 | 10/1993 |
| WO | WO 97/43982 | 11/1997 |
| WO | WO 98/19606 | 5/1998 |
| WO | WO 98/35606 | 8/1998 |
| WO | WO 98/35616 | 8/1998 |
| WO | WO 98/35632 | 8/1998 |
| WO | WO 99/52450 | 10/1999 |
| WO | WO 00/13601 | 3/2000 |
| WO | WO 00/18319 | 4/2000 |
| WO | WO 00/57812 | 10/2000 |
| WO | WO 00/64370 | 11/2000 |
| WO | WO 00/74594 | 12/2000 |
| WO | WO 00/74613 | 12/2000 |
| WO | WO 00/74633 | 12/2000 |
| WO | WO-0106951 A1 | 2/2001 |
| WO | WO 01/26581 | 4/2001 |
| WO | WO 01/39670 | 6/2001 |
| WO | WO 01/45589 | 6/2001 |
| WO | WO-01052729 A2 | 7/2001 |
| WO | WO 01/56499 | 8/2001 |
| WO | WO 02/02031 | 1/2002 |
| WO | WO 02/26108 | 4/2002 |
| WO | WO 02/28312 | 4/2002 |
| WO | WO 02/32284 | 4/2002 |
| WO | WO-0232346 A1 | 4/2002 |
| WO | WO 02/34124 | 5/2002 |
| WO | WO 02/39890 | 5/2002 |
| WO | WO-0239890 A2 | 5/2002 |
| WO | WO-02065921 A1 | 8/2002 |
| WO | WO 02/69781 | 9/2002 |
| WO | WO 02/71953 | 9/2002 |
| WO | WO 02/78552 | 10/2002 |

OTHER PUBLICATIONS

Jacquetin. Utilisation du "TVT" dans la chirurgie . . . J. Gynecol. Obstet. Biol. Reprod. 29: 242-47 (2000).
deTayrac, et al. Prolapse repair by vaginal route using . . . Int. Urogynecol. J. (published online May 13, 2006).
Aldridge, "Transplantation of Fascia for Relief of Urinary Stress Incontinence," *Am. J. Obstet. Gynecol.*, 1942, 44:398-411.
Araki et al., "The Loop-Loosening Procedure for Urination Difficulties After Stamey Suspension of the Vesical Neck," *J. Urol.*, 1990, 144:319-323.
Asmussen and Ulmsten, "Simultaneous Urethro-Cystometry with a New Technique," *Scand. J. Urol. Nephrol.*, 1976, 10:7-11.

Beck and McCormick, "Treatment of Urinary Stress Incontinence with Anterior Colporrhaphy," *Obstetrics and Gynecology*, 1982, 59(3):271-274.
Benderev, "Anchor Fixation and Other Modifications of Endoscopic Bladder Neck Suspension," *Urology*, 1992, 40(5):409-418.
Benderev, "A Modified Percutaneous Outpatient Bladder Neck Suspension System," *J. Urol.*, 1994, 152:2316-2320.
Bergman and Elia, "Three surgical procedures for genuine stress incontinence: Five-year follow-up of a prospective randomized study," *Am. J. Obstet. Gynecol.*, 1995, 173:66-71.
Blaivas and Jacobs, "Pubovaginal Fascial Sling for the Treatment of Complicated Stress Urinary Incontinence," *J. Urol.*, 1991, 145:1214-1218.
Blaivas and Salinas, "Type III Stress Urinary Incontinence: Importance of Proper Diagnosis and Treatment," *American College of Surgeons Surgical Forum*, 1984, 70$^{th}$ Annual Clinical Congress, San Francisco, CA, vol. XXXV, pp. 473-474.
Bryans, "Marlex gauze hammock sling operation with Cooper's ligament attachment in the management of recurrent urinary stress incontinence," *Am. J. Obstet. Gynecol.*, 1979, 133(3):292-294.
Burch, "Urethrovaginal fixation to Cooper's ligament for correction of stress incontinence, cystocele, and prolapse," *Am. J. Obstet. Gynecol.*, 1961, 81(2):281-290.
Choe and Staskin, "Gore-Tex Patch Sling: 7 Years Later," *Urology*, 1999, 54:641-646.
Chopra et al., "Technique of Rectangular Fascial Sling," *Female Urology*, 1996, Raz (ed.), W.B. Saunders Company, Chapter 34, pp. 392-394.
Dargent et al., "Insertion of a sub urethral sling through the obturating membrane in the treatment of female urinary incontinence," *Gynécol. Obstér. Fértil.*, 2002, 30:576-582.
Das and Palmer, "Laparoscopic Colpo-Suspension," *J. Urol.*, 1995, 154:1119-1121.
Decter, "Use of the Fascial Sling for Neurogenic Incontinence: Lessons Learned," *J. Urol.*, 1993, 150:683-686.
Delorme, "The transobturator tape: A minimally invasive procedure for treating female stress urinary incontinence," *Progrés en Urologie*, 2001, 11:1306-1313.
Enzelsberger et al., "Urodynamic and Radiologic Parameters Before and After Loop Surgery for Recurrent Urinary Stress Incontinence," *Acta Obstet. Gynecol. Scand.*, 1990, 69:51-54.
Eriksen et al., "Long-Term Effectiveness of the Burch Colposuspension in Female Urinary Stress Incontinence," *Acta Obstet. Gynecol. Scand.*, 1990, 69:45-50.
Falconer et al., "Clinical Outcome and Changes in Connective Tissue Metabolism After Intravaginal Slingplasty in Stress Incontinent Women," *Int. Urogynecol. J.*, 1996, 7:133-137.
Falconer et al., "Influence of Different Sling Materials on Connective Tissue Metabolism in Stress Urinary Incontinent Women," *Int. Urogynecol. J.*, 2001, (Suppl. 2):S19-S23.
Gilja et al., "A Modified Raz Bladder Neck Suspension Operation (Transvaginal Burch)," *J. Urol.*, 1995, 153:1455-1457.
Gittes and Loughlin, "No-Incision Pubovaginal Suspension for Stress Incontinence," *J. Urol.*, 1987, 138:568-570.
Gruss, "The Obturator Bypass. Indications. Techniques. Outcomes," *Chirurgie*, 1971, 97:220-226.
Guida and Moore, "The Surgeon At Work. Obturator Bypass Technique," *Surgery, Gynecology & Obstetrics*, 1969, pp. 1307-1315.
Handa et al., "Banked Human Fascia Lata for the Suburethral Sling Procedure: A Preliminary Report," *Obstet. Gynecol.*, 1996, 88:1045-1049.
Henriksson and Ulmsten, "A urodynamic evaluation of the effects of abdominal urethrocystopexy and vaginal sling urethroplasty in women with stress incontinence," *Am. J. Obstet. Gynecol.*, 1978, 131:77-82.
Hodgkinson and Kelly, "Urinary Stress Incontinence in the Female. III. Round-ligament technique for retropubic suspension of the urethra," *Obstet. Gynecol.*, 1957, 10:493-499.
Holschneider et al., "The Modified Pereyra Procedure in Recurrent Stress Urinary Incontinence: A 15-Year Review," *Obstet. Gynecol.*, 1994, 83:573-578.

Horbach et al., "A Suburethral Sling Procedure with Polytetrafluoroethylene for the Treatment of Genuine Stress Incontinence in Patients with Low Urethral Closure Pressure," *Obstet. Gynecol.*, 1988, 71:648-652.

Horbach, "Suburethral Sling Procedures," *Urogynecology and Urodynamics-Theory and Practice*, 1996, Williams & Wilkins, pp. 569-579.

Ingelman-Sundberg and Ulmsten, "Surgical Treatment of Female Urinary Stress Incontinence," *Contr. Gynec. Obstet.*, 1983, 10:51-69.

Jeffcoate, "The Results of the Aldridge Sling Operation for Stress Incontinence," *The Journal of Obstetrics and Gynaecology of the British Empire*, 1956, 63:36-39.

Karram and Bhatia, "Patch Procedure: Modified Transvaginal Fascia Lata Sling For Recurrent or Severe Stress Urinary Incontinence," *Obstet Gynecol.*, 1990, 75:461-463.

Kerdiles et al., "Bypass via the Obturator Foramen in Reconstructive Arterial Surgery of the Lower Extremities," *Ann. Chir. Thorac. Cardio-Vasc.*, 1974, 13(4):335-341.

Kerr and Staskin, "The Use of Artificial Material for Sling Surgery in the Treatment of Female Stress Urinary Incontinence," *Female Urology*, 1996, Raz (ed.), W.B. Saunders Company, Chapter 33, pp. 382-391.

Kersey, "The gauze hammock sling operation in the treatment of stress incontinence," *Br. J. Obstet. Gynecol.*, 1983, 90:945-949.

Klutke et al., "The Anatomy of Stress Incontinence: Magnetic Resonance Imaging of the Female Bladder Neck and Urethra," *J. Urol.*, 1990, 143:563-566.

Klutke et al., "Transvaginal Bladder Neck Suspension to Cooper's Ligament: A Modified Pereyra Procedure," *Obstet. Gynecol.*, 1996, 88:294-297.

Korda et al., "Experience with Silastic Slings for Female Urinary Incontinence," *Aust. NZ J. Obstet. Gynaecol.*, 1989, 29:150-154.

Kovac, "Follow-up of the Pubic Bone Suburethral Stabilization Sling Operation for Recurrent Urinary Incontinence (Kovac Procedure)," *J. Pelvic Surgery*, 1999, 5(3):156-160.

Kovac and Cruikshank, "Pubic Bone Suburethral Stabilization Sling for Recurrent Urinary Incontinence," *Obstet. Gynecol.*, 1997, 89:624-627.

Kovac and Cruikshank, "Pubic bone suburethral stabilization sling: a long-term cure for SUI?" *Contemporary OB/GYN*, 1998, 43(2):51-72.

Leach, "Bone Fixation Technique for Transvaginal Needle Suspension," *Urology*, 1988, 31(5):388-390.

Leach et al., "Female Stress Urinary Incontinence Clinical Guidelines Panel Summary Report on Surgical Management of Female Stress Urinary Incontinence," *J. Urol.*, 1997, 158:875-880.

Leval, "Novel Surgical Technique for the Treatment of Female Stress Urinary Continence: Transobturator Vaginal Tape Inside-Out," *European Urology*, 2003, 44:724-730.

Lichtenstein et al., "The Tension-Free Hernioplasty," *Am. J. Surgery*, 1989, 157:188-193.

Loughlin et al., "Review of an 8-Year Experience with Modifications of Endoscopic Suspension of the Bladder Neck for Female Stress Urinary Incontinence," *J. Urol.*, 1990, 143:44-45.

Mahoney and Whelan, "Use of Obturator Foramen in Iliofemoral Artery Grafting: Case Reports," *Annals of Surgery*, 1966, 163(2):215-220.

McGuire, "Abdominal Procedures for Stress Incontinence," *Urologic Clinics of North America*, 1985, 12(2):285-290.

McGuire et al., "Experience with Pubovaginal Slings for Urinary Incontinence at the University of Michigan," *J. Urol.*, 1987, 138:525-526.

McGuire and Lytton, "Pubovaginal Sling Procedure for Stress Incontinence," *J. Urol.*, 1978, 119:82-84.

McIndoe et al., "The Aldridge Sling Procedure in the Treatment of Urinary Stress Incontinence," *Aust. NZ J. Obstet. Gynaecol.*, 1987, 27:238-239.

McKiel, Jr. et al., "Marshall-Marchetti Procedure: Modification," *J. Urol.*, 1966, 96:737-739.

Marshall et al., "The Correction of Stress Incontinence by Simple Vesicourethral Suspension," *J. Urol.*, 2002, 168:1326-1331.

McGuire and Gormley, "Abdominal Fascial Slings," *Female Urology*, 1996, Raz (ed.), W.B. Saunders Company, Chapter 31, pp. 369-375.

Moir, "The Gauze-Hammock Operation," *The Journal of Obstetrics and Gynaecology of the British Commonwealth*, 1968, 75(1):1-9.

Morgan et al., "The Marlex sling operation for the treatment of recurrent stress urinary incontinence: A 16-year review," *Am. J. Obstet. Gynecol.*, 1985, 151:224-226.

Morgan, "A sling operation, using Marlex polypropylene mesh, for treatment of recurrent stress incontinence," *Am. J. Obstet. Gynecol.*, 1970, 106(3):369-376.

Narik and Palmrich, "A simplified sling operation suitable for routine use," *Am. J. Obstet. Gynecol.*, 1962, 84:400-405.

Nichols, "The Mersilene Mesh Gauze-Hammock For Severe Urinary Stress Incontinence," *Obstet. Gynecol.*, 1973, 41(1):88-93.

Nickel et al., "Evaluation of a Transpelvic Sling Procedure With and Without Colpolsuspension for Treatment of Female Dogs With Refractory Urethral Sphincter Mechanism Incompetence," *Veterinary Surgery*, 1998, 27:94-104.

Norris et al., "Use of Synthetic Material in Sling Surgery: A Minimally Invasive Approach," *J. Endocrinology*, 1996, 10(3):227-230.

Novak, "Abdonomovaginal Techniques," *Gynecological Surgical Technique*, 1977, Piccin Editore, Padua, 5 pages.

O'Donnell, "Combined Raz Urethral Suspension and McGuire Pubovaginal Sling for Treatment of Complicated Stress Urinary Incontinence," *J. Arkansas Medical Society*, 1992, 88(8):389.

Parra and Shaker, "Experience with a Simplified Technique for the Treatment of Female Stress Urinary Incontinence," *British Journal of Urology*, 1990, 66:615-617.

Pelosi III and Pelosi, "Pubic Bone Suburethral Stabilization Sling: Laparoscopic Assessment of a Transvaginal Operation for the Treatment of Stress Urinary Incontinence," *Journal of Laparoendoscopic & Advanced Surgical Techniques*, 1999, 9(1):45-50.

Pelosi II and Pelosi III, "New transobturator sling reduces risk of injury," *OBG Management*, 2003, pp. 17-37.

Penson and Raz, "Why Anti-incontinence Surgery Succeeds or Fails," *Female Urology*, 1996, Raz (ed.), W.B. Saunders Company, Chapter 41, pp. 435-442.

Pereyra et al., "Pubourethral Supports in Perspective: Modified Pereyra Procedure for Urinary Incontinence," *Obstet Gynecol.*, 1982, 59:643-648.

Petros and Ulmsten, "An analysis of rapid pad testing and the history for the diagnosis of stress incontinence," *Acta Obstet. Gynecol. Scand.*, 1992, 71:529-536.

Petros and Ulmsten, "An Anatomical Basis for Success and Failure of Female Incontinence Surgery," *Scand. J. Urol. Nephrol.*, 1993, (Suppl. 3):55-60.

Petros and Konsky, "Anchoring the midurethra restores bladder-neck anatomy and continence," *The Lancet*, 1999, 354:997-998.

Petros et al., "The Autogenic Ligament Procedure: A Technique for Planned Formation of an Artificial Neo-Ligament," *Acta Obstet. Gynecol. Scand.*, 1990, 69(Suppl. 153):43-51.

Petros and Ulmsten, "Bladder Instability in Women: A Premature Activation of the Micturition Reflex," *Neurourology and Urodynamics*, 1993, 12:235-239.

Petros and Ulmsten, "The Combined Intravaginal Sling and Tuck Operation. An Ambulatory Procedure for Cure of Stress and Urge Incontinence," *Acta Obstet. Gynecol. Scand.*, 1990, 69(Suppl. 153):53-59.

Petros and Ulmsten, "Cough Transmission Ratio: An Indicator of Suburethral Vaginal Wall Tension Rather than Urethral Closure?" *Acta Obstet. Gynecol. Scand.*, 1990, 69(Suppl. 153):37-38.

Petros and Ulmsten, "Cure of Stress Incontinence by Repair of External Anal Sphincter," *Acta. Obstet. Gynecol Scand.*, 1990, 69(Suppl. 153):75.

Petros and Ulmsten, "Cure of Urge Incontinence by the Combined Intravaginal Sling and Tuck Operation," *Acta Obstet. Gynecol. Scand.*, 1990, 69(Suppl. 153)61-62.

Petros, "Development of Generic Models for Ambulatory Vaginal Surgery—a Preliminary Report," *Int. Urogynecol. J.*, 1998, 9:19-27.

Petros and Ulmsten, "The Development of the Intravaginal Slingplasty Procedure: IVS II—(with bilateral "tucks")," *Scand. J. Urol. Nephrol.*, 1993, Suppl. 153:61-67.

Petros and Ulmsten, "The Free Graft Procedure for Cure of the Tethered Vagina Syndrome," *Scand. J. Urol. Nephrol.*, 1993, Suppl. 153:85-87.

Petros and Ulmsten, "Further Development of the Intravaginal Slingplasty Procedure—IVS III—(with midline "tuck")," *Scand. J. Urol. Nephrol.*, 1993, Suppl. 153:69-71.

Petros and Ulmsten, "The Further Development of the Intravaginal Slingplasty Procedure: IVS IV—(with "double-breasted" unattached vaginal flap repair and "free" vaginal tapes)," *Scand. J. Urol. Nephrol.*, 1993, Suppl. 153:73-79.

Petros and Ulmsten, "An Integral Theory of Female Urinary Incontinence," *Acta Obstet. Gynecol. Scand.*, 1990, 69(Suppl.153):7-31.

Petros and Ulmsten, "The Intravaginal Slingplasty Procedure: IVS VI—further development of the "double-breasted" vaginal flap repair—attached flap," *Scand. J. Urol. Nephrol.*, 1993, Suppl. 153:81-84.

Petros and Ulmsten, "Non Stress Non Urge Female Urinary Incontinence—Diagnosis and Cure: A Preliminary Report," *Acta Obstet. Gynecol. Scand.*, 1990, 69(Suppl. 153):69-70.

Petros and Ulmsten, "Part 1: Theoretical, Morphological, Radiographical Correlations and Clinical Perspective," *Scand. J. Urol. Nephrol.*, 1993, Suppl. 153:5-28.

Petros and Ulmsten, "Part II: The Biomechanics of Vaginal Tissue and supporting Ligaments with Special Relevance to the Pathogenesis of Female Urinary Incontinence," *Scand. J. Urol. Nephrol.*, 1993, Suppl. 153:29-40.

Petros and Ulmsten, "Part III: Surgical Principles Deriving from the Theory," *Scand. J. Urol. Nephrol.*, 1993, Suppl. 153:41-52.

Petros and Ulmsten, "Part IV: Surgical Applications of the Theory—Development of the Intravaginal Sling Plasty (IVS) Procedure," *Scand. J. Urol. Nephrol.*, 1993, Suppl. 153:53-54.

Petros and Ulmsten, "Pinch Test for Diagnosis of Stress Urinary Incontinence," *Acta Obstet. Gynecol. Scand.*, 1990, 69(Suppl. 153):33-35.

Petros and Ulmsten, "The Posterior Fornix Syndrome: A Multiple Symptom Complex of Pelvic Pain and Abnormal Urinary Symptoms Deriving from Laxity in the Posterior Fornix of Vagina," *Scand. J. Urol. Nephrol.*, 1993, Suppl. 153:89-93.

Petros and Ulmsten, "Pregnancy Effects on the Intravaginal Sling Operation," *Acta Obstet. Gynecol. Scand.*, 1990, 69(Suppl.153):77-78.

Petros and Ulmsten, "The Role of a Lax Posterior Vaginal Fornix in the Causation of Stress and Urgency Symptoms: a Preliminary Report," *Acta Obstet. Gynecol. Scand.*, 1990, 69(Suppl. 153):71-73.

Petros and Ulmsten, "The Tethered Vagina Syndrome, Post Surgical Incontinence and I-Plasty Operation for Cure," *Acta Obstet. Gynecol Scand.*, 1990, 69(Suppl.153):63-67.

Petros and Ulmsten, "The Tuck Procedure: A Simplified Vaginal Repair for Treatment of Female Urinary Incontinence," *Acta Obstet. Gynecol. Scand.*, 1990, 69(Suppl.153):41-42.

Petros and Ulmsten, "Urethral Pressure Increase on Effort Originates From Within the Urethra, and Continence From Musculovaginal Closure," *Neurourology and Urodynamics*, 1995, 14:337-350.

Rackley, "Synthetic slings: Five steps for successful placement—Follow these steps to insert Transvaginal/Percutaneous slings using vaginal approach alone," *Urology Times*, 2000, 28:46-49.

Rackley et al., "Tension-free Vaginal Tape and Percutaneous Vaginal Tape Sling Procedures," *Techniques in Urology*, 2001, 7(2):90-100.

Raz, "Modified Bladder Neck Suspension for Female Stress Incontinence," *Urology*, 1981, 17(1):82-85.

Raz et al., "Urological Neurology and Urodynamics," *J. Urol.*, 1992, 148:845-850.

Jeter, "The Social Impact of Urinary Incontinence," *Female Urology*, Raz (ed.), W. B. Saunders Company, 1996, Chapter 7, pp. 80-86.

Richardson et al., "Delayed Reaction to the Dacron Buttress Used in Urethropexy," *J. Reproductive Med.*, 1984, 29(9):689-692.

Ridley, "Appraisal of the Goebell-Frangenheim-Stoeckel sling procedure," *Am. J. Obstet. Gynecol.*, 1966, 95(5):714-721.

Sheiner et al., "An unusual complication of obturator foramen arterial bypass," *J. Cardiovasc. Surg.*, 1969, 10(4):324-328.

Sirls and Leach, "Use of Fascia Lata for Pubovaginal Sling," *Female Urology*, 1996, Raz (ed.). W.B. Saunders Company, Chapter 32, pp. 376-381.

Sloan and Barwin, "Stress Incontinence of Urine: A Retrospective Study of the Complications and Late Results of Simple Suprapubic Suburethral Fascial Slings," *J. Urol.*, 1973, 110:533-536.

Spencer et al., "A Comparison of Endoscopic Suspension of the Vesical Neck with Suprapubic Vesicourethropexy for Treatment of Stress Urinary Incontinence," *J. Urol.*, 1987, 137:411-415.

Stamey, "Endoscopic Suspension of the Vesical Neck for Urinary Incontinence in Females," *Annals of Surgery*, 1980, 192(4):465-471.

Stanton, "Suprapubic Approaches for Stress Incontinence in Women," *J. Am. Geriatrics Soc.*, 1990, 38(3):348-351.

Staskin et al., "The Gore-tex sling procedure for female sphincteric incontinence: indications, technique, and results," *World J. Urol.*, 1997, 15:295-299.

Stothers et al., "Anterior Vaginal Wall Sling," *Female Urology*, 1996, Raz (ed.), W.B. Saunders Company, Chapter 35, pp. 395-398.

Ulmsten et al., "An Ambulatory Surgical Procedure Under Local Anesthesia for Treatment of Female Urinary Incontinence," *Int. Urogynecol. J.*, 1996, 7:81-86.

Ulmsten et al., "Different Biochemical Composition of Connective Tissue in Continent and Stress Incontinent Women," *Acta Obstet. Gynecol. Scand.*, 1987, 66:455-457.

Ulmsten, "Female Urinary Incontinence—A Symptom, Not a Urodynamic Disease. Some Theoretical and Practical Aspects on the Diagnosis and Treatment of Female Urinary Incontinence," *Int. Urogynecol. J.*, 1995, 6:2-3.

Ulmsten and Petros, "Intravaginal Slingplasty (IVS): An Ambulatory Surgical Procedure for Treatment of Female Urinary Incontinence," *Scand. J. Urol. Nephrol.*, 1995, 29:75-82.

Ulstem et al., "A Multicenter Study of Tension-Free Vaginal Tape (TVT) for Surgical Treatment of Stress Urinary Incontinence," *Int. Urogynecol. J.*, 1998, 9:210-213.

Ulmsten et al., "A three-year follow up of tension free vaginal tape for surgical treatment of female stress urinary incontinence," *Br. J. Obstet. Gynecol.*, 1999, 106:345-350.

Ulmsten et al., "The unstable female urethra," *Am. J. Obstet. Gynecol.*, 1982, 144:93-97.

Webster and Kreder, "Voiding Dysfunction Following Cystourethropexy: Its Evaluation and Management," *J. Urol.*, 1990, 144:670-673.

Winter, "Peripubic Urethropexy for Urinary Stress Incontinence In Women," *Urology*, 1982, 20(4):408-411.

Woodside and Borden, "Suprapubic Endoscopic Vesical Neck Suspension for the Management of Urinary Incontinence in Myelodysplastic Girls," *J. Urol.*, 1986, 135:97-99.

Zacharin and Hamilton, "Pulsion Enterocele: Long-Term Results of an Abdominoperineal Technique," *Obstet. Gynecol.*, 1980, 55(2):141-148.

Zacharin, "The suspensory mechanism of the female urethra," *J. Anat.*, 1963, 97(3):423-427.

U.S. Appl. No. 60/362,806, filed Mar. 7, 2002.
U.S. Appl. No. 60/380,797, filed May 14, 2002.
U.S. Appl. No. 60/402,007, filed Aug. 8, 2002.
U.S. Appl. No. 60/414,865, filed Sep. 30, 2002.

* cited by examiner

METHOD FOR TREATING URINARY INCONTINENCE IN WOMEN AND IMPLANTABLE DEVICE INTENDED TO CORRECT URINARY INCONTINENCE

CROSS REFERENCE TO RELATED FOREIGN APPLICATIONS

This application is a continuation of U.S. application Ser. No. 10/455,465, filed Jun. 4, 2003 now abandoned, which is a divisional of U.S. application Ser. No. 10/092,069, filed Mar. 5, 2002, now U.S. Pat. No. 6,638,211, which is a continuation of International Application Serial No. PCT/FR01/02120, filed Jul. 3, 2001, which claims priority from French Patent Application Serial No. 00.08706, filed Jul. 5, 2000, and is a continuation-in-part of U.S. application Ser. No. 09/661,620, filed on Sep. 14, 2000 now abandoned. This application claims priority to each of these prior applications. In addition, the disclosure of these prior applications are considered part of (and are incorporated by reference in) the disclosure of this application.

The invention relates to a method for treating urinary incontinence in women. It also relates to an implantable device intended to correct urinary incontinence in women. The said device is more particularly suited to the treatment of stress urinary incontinence.

Various types of device have been proposed for treating phenomena of urinary incontinence in women.

Thus, for example, document U.S. Pat. No. 5,899,909 describes a tape of constant width, made of a material of the meshed or knitted polypropylene type ensuring fibroblast colonization and thus anchorage into the tissues along its entire length. Once an incision has been made in the wall of the vagina this tape is positioned under the urethra, the tape being led upwards on each side of the bladder to be anchored into the abdominal wall.

The method of fitting this tape is relatively tricky. Specifically, the needles being led vertically up alongside the bladder may not only pierce the latter, but may above all pierce the iliac artery or even the small intestine. In consequence, it is essential that cystoscopy be performed during the intervention.

Document WO 98/35632 describes a device in the form of a tape, the central region of which is wider than the body of the tape, the assembly being made of a biocompatible material, particularly a woven material, allowing for fibroblast colonization.

As before, each of the ends of the tape is led up alongside the bladder to be secured at the abdominal wall or, more specifically, in the bone of the pubis. Thus, the same drawbacks as before may be encountered.

One of the objects of the invention is to artificially reconstruct the pelvic fascia by fitting tapes aimed at restoring, as faithfully as possible, the effective and natural situation of the endo-pelvic fascia, in its role of fibrous plug obturating the urogenital opening, the said fascia resting on either side of the said opening on the floor of the lifting muscles.

Another of the stated objects of the present invention lies in solving the problems associated with subsequent surgical re-intervention in the region of the urethra; given the fact that the tapes proposed by the Prior Art are made, along their entire length, of a material capable of being colonized by fibroblasts, the problem arises of performing an intervention in this region if the tape, because of the fibroblast colonization, is anchored to the periurethral wall. A solution to this new problem is all the more important now that it has been found that the phenomenon of urinary incontinence may evolve to the fitting of an artificial sphincter. A problem such as this is neither disclosed nor suggested in the Prior Art.

Furthermore, the literature has described possible phenomena of the migration of the substance of which the tape is made, particularly polypropylene, into the viscera.

In order to solve all of these problems, the Applicant is proposing a method and an implantable device, intended to correct urinary incontinence in women.

This method for treating urinary incontinence in women comprises the following steps:

making a mediane paraurethral incision, practically in the middle third of the urethra, measured from the meatus, so as to allow the passage of a tape between the Alban fascia and the periurethral fascias;

extending each of the free ends of the said tape in the region of the two obturator foramen of the iliac wing and leading them out into the groin opposite the corresponding foramen so that they essentially form a V shape, the point of which V passes under the urethra without changing the position thereof.

In other words, and contrary to the surgical techniques employed in the state of the art, the tape is not led up alongside the bladder to form a U and thus be situated in close proximity to vital organs, but is on the contrary diverted from the bladder to form a V. Hence, no risk of damaging the bladder, the iliac artery or the small intestine is run. In consequence, it is not necessary to perform cystoscopy during the intervention.

According to the invention, in order to make it easier to fit the tape which acts as an implant, a space is made between, on the one hand, the Alban fascia, the perineal muscular plane and the anterior insertion of the puborectal muscle and, on the other hand, the periurethral fascias.

According to an advantageous version of the invention, the central region of the tape or implant, which region is intended to be inserted between the Alban fascia and the periurethral fascias, is coated with a substance capable of preventing any adhesion of the said fascias to the tape.

Thus it becomes possible to avoid any cell growth on the tape between the wall of the vagina and the wall of the urethra, hence avoiding any anchorage of the tape in this region and thus to allow subsequent surgical re-intervention. Furthermore, coating it with such a substance in the region of the urethra makes it possible to avoid any migration of polypropylene into the viscera.

The device according to the invention is characterized in that it is in the form of a tape of which the central region, intended to be inserted between the Alban fascia and the periurethral fascia, is coated with a substance capable of preventing any adhesion of the said fascias to the tape.

In a first embodiment, the substance that prevents adhesion of the fascias to the tape is silicone.

In a second embodiment, the substance is made of vegetable or animal growth factors.

Of course, any substance capable of avoiding the adhesion of the fascias to the tape may be envisaged.

The tape is coated on both side, advantageously on one side.

Furthermore, the tape is made of any materials such as those known to those skilled in the art and, in particular but without applying any limitation, any material chosen from the group containing polyethylene and polypropylene.

According to another feature, when the tape is made of polypropylene, the polypropylene is either meshed or knitted or alternatively is in the form of sprayed fibres. Nevertheless, the tape can also be made of absorbable material.

In one advantageous embodiment, the central region of the tape is not as wide as the rest of the tape and this is so as to limit the area of contact in the region of the Alban fascia and of the periurethral fascia.

Furthermore, and according to another feature, each of the ends of the tape has a tapered point intended to be anchored in the groin facing the corresponding obturator foramen.

According to a preferred embodiment, the tape has a length equal to 60 cm and a width equal to 2.5 cm, and has a central region which is not as wide, being 1 cm wide over a length equal to 3 cm. Advantageously, the central region has a length equal to 15 mm.

The invention and its ensuing advantages will emerge better from the following example in support of the appended figures.

Figure 1:
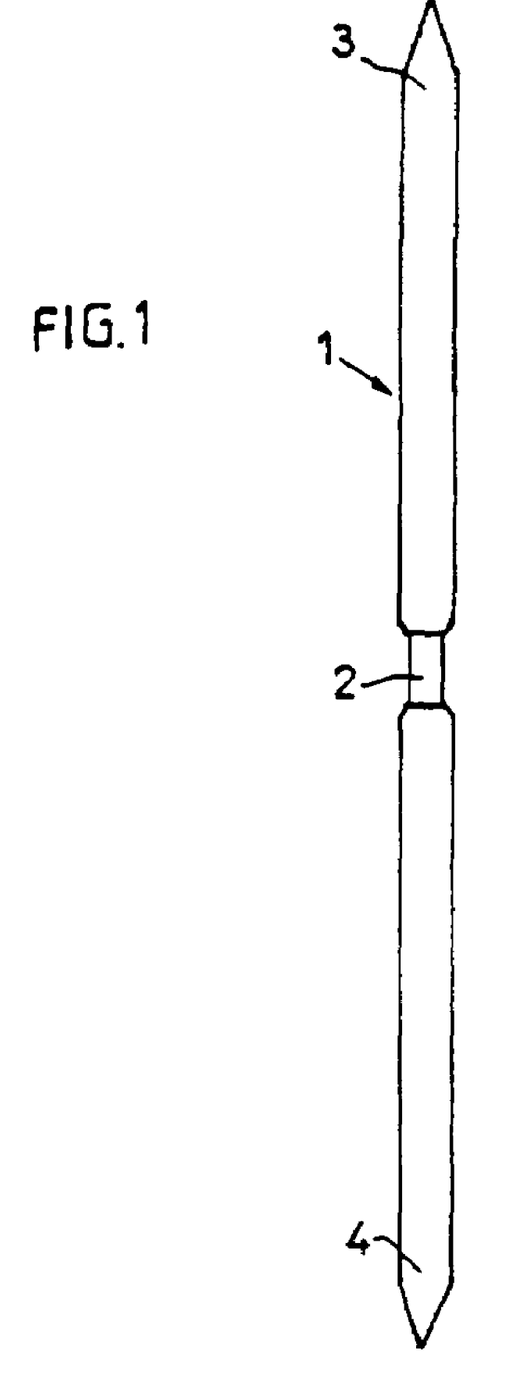
FIG. 1 is a diagrammatic depiction of the tape of the invention.

As shown in FIG. 1, the device of the invention is in the form of a tape (1) of a length equal to 60 cm and of a width equal to 2.5 cm. This tape is made, along its entire length, of sprayed polypropylene fibres.

According to an advantageous feature, the tape has, at its centre (2), a narrowing of length equal to 3 cm and of width equal to 1 cm, this portion being coated on both sides with a silicone-containing substance. Furthermore, each of its free ends (3, 4) is tapered.

Fitting the device requires mini-invasive surgery, the main steps of which are described hereinafter.

First of all, a mediane paraurethral incision is made in the region of the middle third of the urethra.

One of the two obturator foramen, and more specifically the lower internal part is then identified by a finger slipped into the vaginal incision and an incision is made in the perineal skin opposite it, and so in the groin, so as to form an orifice through which an Emmet needle is then passed. This needle is introduced through this cutaneous incision firstly perpendicular to the perineum for about 15 mm (passing through the internal obturator muscle as far as just outside the ischiopubic branch), then the needle is allowed to describe its curvature, guided in this by the finger introduced opposite the obturator muscle through the vaginal incision. The pointed end of the tape is then slipped into the eye of the needle, emerging from the said vaginal incision, then pulled back through the thickness of muscle, the retractor and the internal obturator up to the surface of the skin.

The tape is then placed between the Alban fascia and the periurethral fascias to position it in such a way that its central region, coated with silicone as appropriate, faces the said fascias. The tape is positioned without pulling behind the urethra.

An incision is then made in the perineal skin facing the second obturator foramen, into which incision an Emmet needle is inserted. The free end of the tape is then slipped into the eye of the needle which is pulled back in the same way as before.

The excess tape is then cut off flush with the skin then the skin is immobilized to disconnect it from the tape. The incision is finally closed with a stitch of quickly absorbable suture.

Figure 2:
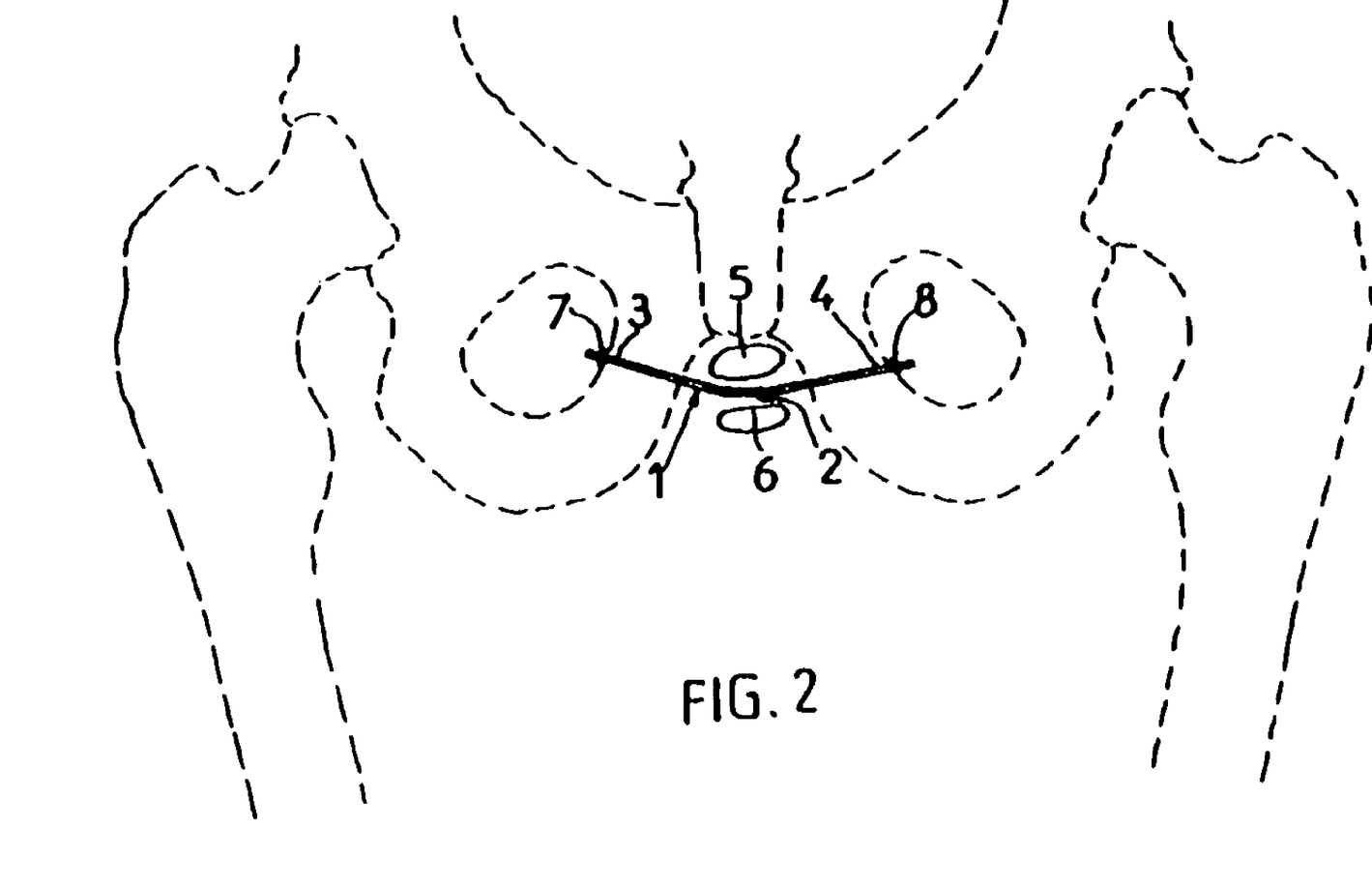
FIG. 2 is a diagrammatic depiction of the position of the tape after fitting.

FIG. 2 diagrammatically depicts the position, in cross section, of the tape after it has been fitted. As shown in this figure, once in place, the tape adopts the shape of a V, the branches of which are very far apart.

Furthermore, it can also be seen that when the tape according to one of the advantageous embodiments of the invention is used, the silicone-coated segment of the tape is positioned between the uterus (5) and the vagina (6), while its ends (3, 4) are secured in the region of the groin (7, 8) facing the obturator foramen.

Thanks to the robustness and texture of the tape, tension can be strong without there being any risk of rupture. The tape is positioned under the control of sight without employing cystoscopy. It is essential that there be no pulling on this tape which has to be slipped down under the urethra without altering the position thereof.

It is apparent from the foregoing that the method according to the invention for treating urinary incontinence in women differs from the methods proposed in the state of the art through the simplicity of fitting of the tape, using mini-invasive surgery. Furthermore, it provides the urethra with firm suspension while at the same time maintaining a certain degree of flexibility and, most of all, keeping the vital organs in the vicinity relatively far away from the said tape. Furthermore, it plays a part in reconstructing the endopelvic fascia.

The invention claimed is:

1. A method for treating urinary incontinence in a woman, said method comprising:
   (a) making a vaginal incision in the region of the middle third of the urethra measured from the meatus, and
   (b) positioning a tape under the urethra of said woman such that one portion of said tape extends from under the urethra through one obturator foramen of said woman and another portion of said tape extends from under the urethra through the other obturator foramen of said woman.

2. The method of claim 1, wherein positioning the tape further comprises using a curved needle to extend one portion of said tape from under the urethra through one obturator foramen of said woman.

3. The method of claim 2, further comprising inserting a finger into said vaginal incision and guiding said curved needle to said vaginal incision.

4. The method of claim 2, further comprising inserting a tapered end of said tap into an eye of said curved needle.

5. The method of claim 1, further comprising cutting the ends of said tape flush with a skin surface of said woman.

6. The method of claim 5, further comprising tapering the ends of said tape before cutting the ends flush with the skin surface of said woman.

7. A method for treating urinary incontinence in a woman, said method comprising:
   (a) making a vaginal incision in the region of the middle third of the urethra measured from the meatus, and
   (b) positioning an elongated implant under the urethra of said woman such that one portion of said implant extends from under the urethra through one obturator foramen of said woman and another portion of said implant extends from under the urethra through the other obturator foramen of said woman.

8. A method for treating urinary incontinence in women, comprising:
   making a median paraurethral incision, practically in the middle third of the urethra, measured from the meatus, so as to allow the insertion of an implant;
   inserting at least a portion of the implant through the incision; and
   extending each free ends of said implant respectively into a region of two obturator foramen of the iliac wing and leading them out towards the groin opposite the corresponding foramen so that they essentially form a V shape, the point of which V passes under the urethra without changing the position thereof.

9. The method of claim 8, further comprising forming a space within the tissue to accommodate a portion of the implant.

10. The method of claim 8, further comprising providing at least a portion of the implant that is coated with an adhesion preventing material and positioning the coated portion proximate the urethra.

11. A method for treating urinary incontinence in women, comprising:

making a median paraurethral incision, practically in the middle third of the urethra, measured from the meatus;

passing an implant through the incision;

directing a first end of the implant towards an first obturator foramen;

directing a second end of the implant towards an opposite obturator foramen;

securing the ends of the implant so that the implant essentially forms a V shape, the center of which passes under the urethra without changing the position thereof.

\* \* \* \* \*

UNITED STATES PATENT AND TRADEMARK OFFICE
CERTIFICATE OF CORRECTION

PATENT NO. : 7,621,864 B2
APPLICATION NO. : 11/040698
DATED : November 24, 2009
INVENTOR(S) : Suslian et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1344 days.

Signed and Sealed this

Fourteenth Day of December, 2010

David J. Kappos
*Director of the United States Patent and Trademark Office*